May 27, 1969 J. S. SWEET Plant Pat. 2,889
POINSETTIA PLANT
Filed Feb. 13, 1967
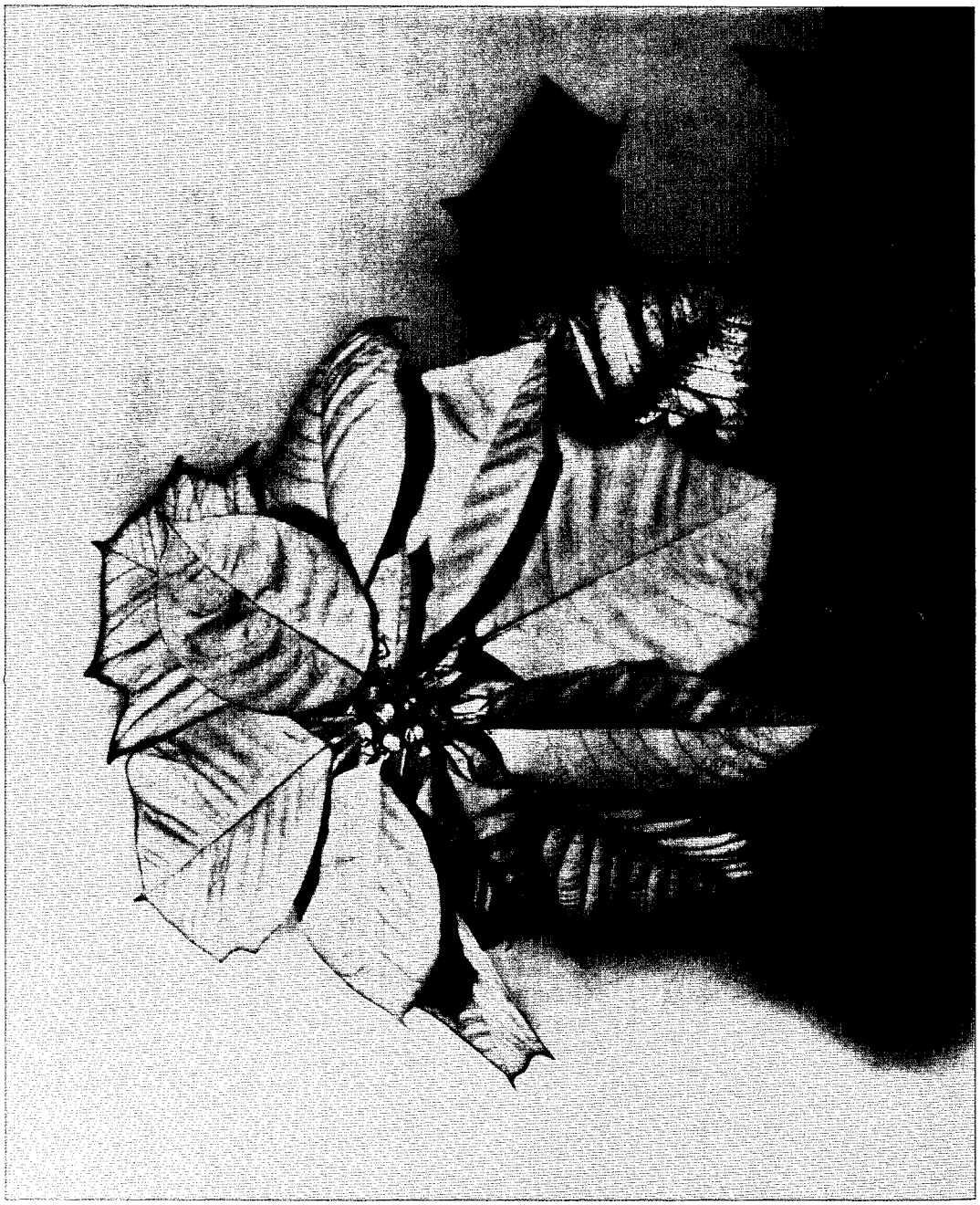
Jack S. Sweet
by
Myron P. Laughlin.
Attny.

United States Patent Office

Plant Pat. 2,889
Patented May 27, 1969

2,889
POINSETTIA PLANT

Jack S. Sweet, St. Petersburg, Fla., assignor to Earl J. Small Orchids, Inc., Pinellas Park, Fla., a corporation of Florida

Filed Feb. 13, 1967, Ser. No. 615,854
Int. Cl. A01h *5/02*
U.S. Cl. Plt.—86 1 Claim

This present invention relates to a distinctively new poinsettia plant of the species *Euphorbia pulcherrima* now discovered and asexually reproduced.

This poinsettia plant invention represents improvement in *Euphorbia pulcherrima* plants over the prior art in that, by natural growth changes it incorporates in the plant parts, which have heretofore arranged in a ragged open structure, to a compact, stronger, more brilliant mass, extending its benefits to the plant cell structure to simultaneously increase plant strength and decorative values, thus extending the useful life of the poinsettia and its value to the public.

This present poinsettia plant is a cross-bred descendant resultant from two formerly discovered poinsettia plant varieties, one partially known and recognized as a common commercial breed, and the other conceived by natural mating and remating still another known commercial descendant by cross pollenation from known breeds to include certain other improved cellular structure characteristics for such a plant.

It should be understood that asexual reproduction of poinsettia plants to produce a new, distinctive and completely naturally stable form which can be depended on to consistingly reproduce in external and internal structure from new cuttings, is a matter of years of patient scientific research and experimentation involving large expenditures of both time and money applied for a known goal. While accidental discoverey of "sports" on the other hand has been the common source of many former "inventions" in *Euphorbia pulcherrima*; the matter of benefitting the whole public has also been largely accidental since cuttings from these sports may, and often do, revert promptly to the original parent, with disappointing results to those who have purchased cuttings in a desire for the improved characteristics of the allegedly new breed. It should be further understood that growing plants, and their sports, are now often treated chemically to stunt their growth, in an attempt to manufacture plant strength. The present invention breeds into the root stem and plant structure the necessary strength for sturdy plants without expensive, often erratic, results of chemical after-treatment. Thus my new plant meets the need for a consistently strong shipment structure, capable of withstanding rough treatment, to at all times deliver to the public a beautifully erect plant decoration of longer useful life than heretofore known, a new plant which by its strength and longevity often reduces the actual cost of a whole decorative scheme to the final consumer since former horticultural designers have often advised that a replacement background of other growths always be provided for poinsettia plantings since rapid fading and drooping of previous poinsettia plants quickly reduced their decorativeness.

The improved appearance of this new plant, its greater sturdiness of structure and its lack of former "ragged-tatters" bloom will be apparent on examination of the hereto attached photographs. The colors in these photographs and in the appended descriptive matter are coded from the Nickerson Color Fan (Munsell Color Co.) except where common dictionary significance will be obvious. The description and photographs are taken from specimens asexually reproduced under my direction through natural growth in greenhouses at Pinellas Park in Florida.

*Parentage (seedling)*

*Seed parent.*—An unnamed seedling designated herein and in my records only as #10 (final descendant from a cascade of cross-breeding based on commercial varieties "Barbara Ecke Supreme" (P.P. #1,055) and "New Ecke White").

*Pollen parent.*—The Barbara Ecke Supreme plant as commercially sold.

*Growth habit of my improved plant*

Upright, compact, sturdy stems of increased caliber with shortened height growth characteristics and polyploid type cell structure as a natural phenomenon without chemical application. Self branching eliminated while the new type leaves are characteristically on short internodes. A whole new plant structure producing a self supporting rigid plant growth withstanding shipment without external support.

*Root foundation*

The rooting characteristics of my new poinsettia plant are at once faster growing and stronger in growth than many former commercial plants. New thickened cell structure appears in the roots, and other parts, so that, the whole plant is of great strength with much greater resistance to root rot and other detrimental organism attack.

*Bloom season—Timing of full bloom*

Late November and December bloom appears to be the natural cycle for this improved poinsettia plant, thus this new plant provides a natural timing in step with maximum public use and commercial demand, providing much increased plant value to producer and consumer alike.

*Foliage in general*

The new leaves are alternate, medium size (compacting at about 4 to 6" in length). These new leathery type leaves have normal coriaceous structures borne on petioles shorter than formerly characteristic of such plants. Leaf blades vary in plane from very broadly oblong to broad ovate outline and have deltoid acuminate apices with several prominent teeth at the outer ends of certain lateral veins. These teeth occurring principally on the apical half of the leaf blade. The leaf color, new foliage, is slightly darker than "Strong Green" (#5G—4/7) on the upper side and "Strong Green" (#5G—5/8 Nickerson) on the leaf underside.

*Improved inflorescence*

Bracts are most distinctive, being both very broad and very brilliantly red (Nickerson "Strong Red" #5R—4/12) upper side and ("Strong Red" #2.5R—5/12) on the lower side while the new much closer set of these bracts on shorter petioles combined with their increased broadness of bract form provides overlap to give a substantially solid bract involucre wherein the dense overlay provides a substantially planular total of great beauty. This new plant structure with its compact bract arrangement does much to eliminate the ragged, tattered appearance so detractive to true beauty in former poinsettias. Increasing the beauty of my new plant's coloration, the underside of the lowermost bracts have a "washed," "suffused" appearance: as if a light yellowish-pink had been applied (#2.5YR—9/3 Nickerson) while, since the lower bracts are wider, with acute teeth toward their apices, they now assume a novel form approximating the shape of a broad oak leaf. The added body and size and greater strength of these bracts also add support to the whole structure. The tiniest bracts I have found, when very new, show a pale yellowish color on red with pale greenish-yellow that more or less matches the color of the true flower at the bract center, thus forming a most pleasing blending whole.

*Flowers*

Flower bloom in my new plant presents a compact tight cluster slowly maturing on short peduncles that do not spread out with age, so that a more compact whole is presented contrasting strongly with the usual split, increasing large, center common to former such products. The flower size of my new plant characteristically approaches only one quarter inch in size while ranging in color from strong greenish-yellow (10Y—6/7 Nickerson) to "Vivid Yellow" (5Y—8/12) at their tops. Nectar cups are now provided of "Vivid Yellow" (5Y—8/12) while the new plant stamens are "Dark Red" (5R—3/7) with the pollen itself is again "Vivid Yellow" (5Y—8/12). The flower portions of my new plant then are small compact color forms to vividly accentuate the startling solid red mass of the bract involucre, thus providing a solid inherent inflorescence of great beauty.

*Summarizing*

My new hybrid poinsettia plant now provides a new and greatly improved appearance of solid colored mass arranged about contrasting small flowers, all accentuated by deep green leaves. This crown inflorescence is mounted on a compact sturdy plant structure of controlled optimum height. My new form bracts (where the red mass must form) are broader, richer in color, and more closely set tight about the reduced center flower whose bright contrast emphasizes the vivid red. These new bracts being of much greater broadness and substance than formerly obtained are so closely set in overlapping relationship that they provide at once a close knit color scheme. Thus my new plant provides a solid self supporting bloom crowning a self supporting, color accentuated body, and the entire plant is compact, strong, long lived, for greater value to its producers, its sellers, and to the whole public enjoying its greatly improved appearance over a longer life span. My new poinsettia plant also provides improved cellular structure, and root structure, while the leaf, root, bract and flowers have all been made into a more coherent whole, improved in many ways over the poinsettias of the past as those specially skilled in the art will recognize.

I claim:

1. A new and distinct variety of poinsettia plant substantially as illustrated and described, characterized by a compactly formed, vivid red bract involucre having very broad bracts widened and toothed as in an oak leaf on the lower layer and with very broad ovate bracts on short petioles in dense overlap about tiny center growth bracts ringing tightly set flowers with nectar caps and stamens of vivid yellow, the entire bract involucre being of thick, leathery, polyploid type cell structure and having as part of its natural growth, thick, and long lasting leaves set close together on an extremely sturdy upright stem of naturally large caliper with short internodes, the whole presenting a complete inflorescence in coherent planular formation, with densely overlapped and intersupporting vivid red bract involucre on a self supporting heavy trunk.

No references cited.

ROBERT E. BAGWILL, *Primary Examiner.*